United States Patent [19]

Bodmer et al.

[11] Patent Number: 5,219,996
[45] Date of Patent: Jun. 15, 1993

[54] RECOMBINANT ANTIBODIES AND METHODS FOR THEIR PRODUCTION IN WHICH SURFACE RESIDUES ARE ALTERED TO CYSTEINE RESIDUES FOR ATTACHMENT OF EFFECTOR OR RECEPTOR MOLECULES

[75] Inventors: Mark W. Bodmer, Oxfordshire; John R. Adair, High Wycombe; Nigel R. Whittle, Surrey; Alan H. Lyons, Maidenhead; Raymond J. Owens, Henley-on-Thames, all of United Kingdom

[73] Assignee: Celltech Limited, Berkshire, United Kingdom

[21] Appl. No.: 353,634

[22] PCT Filed: Sep. 5, 1988

[86] PCT No.: PCT/GB88/00729
§ 371 Date: Jul. 3, 1989
§ 102(e) Date: Jul. 3, 1989

[87] PCT Pub. No.: WO89/01782
PCT Pub. Date: Mar. 9, 1989

[30] Foreign Application Priority Data

Sep. 4, 1987 [GB] United Kingdom ................ 8720833

[51] Int. Cl.⁵ .................. C07K 15/28; A61K 39/395; C12P 21/08
[52] U.S. Cl. ............................. 530/387.3; 530/387.1; 530/391.1; 530/391.5; 424/85.8; 424/85.91; 435/69.6; 435/70.21; 435/172.2; 435/172.3; 435/240.27; 435/320.1
[58] Field of Search ................. 424/85.8, 85.91; 435/69.1, 69.6, 70.21, 172.1, 172.2, 172.3, 240.27, 320.1; 530/387–389, 387.1, 387.3, 391.5, 391.1

[56] References Cited

U.S. PATENT DOCUMENTS 4,751,077  6/1988  Bell et al. ........................... 424/85

FOREIGN PATENT DOCUMENTS 0171496  2/1986  European Pat. Off. .
0173494  3/1986  European Pat. Off. .
0239400  9/1987  European Pat. Off. .
8601533  3/1986  PCT Int'l Appl. .
8702671  5/1987  PCT Int'l Appl. .

OTHER PUBLICATIONS

Lyons et al, "Site-specific attachment to recombinant antibodies via introduced surface cysteine residues", Protein Engineering vol. 3, No. 8, 1990, pp. 703–708.
Kabat, "Investigation and Exploitation of Antibody Combining Sites", Plenum Press, 1985, pp. 3–22.
Davies et al, "Investigation and Exploitation of Antibody Combining Sites", Plenum Press, 1985, pp. 51–60.
Novotny et al, "Antigenic determinants in proteins coincide with regions accessible to large probes (antibody domains)", Proc. Natl. Acad. Sci. vol. 83, Jan. 1986, pp. 226–230.
Connolly, "Solvent-Accessible Surfaces of Proteins and Nucleic Acids", Science, Aug. 1983, vol. 221, pp. 709–713.

*Primary Examiner*—David L. Lacey
*Assistant Examiner*—Robert D. Budens
*Attorney, Agent, or Firm*—Cushman, Darby & Cushman

[57] ABSTRACT

The present invention provides an altered antibody molecule wherein a residue in a surface pocket on the molecule has been changed to a cysteine residue to introduce a thiol group in the surface pocket and a process for its production by recombinant DNA technology.

10 Claims, 4 Drawing Sheets

FIG. IA

```
                                                              4 1
                                                              * *
G4ch1    ASTKGPSVFP LAPCSRSTSE STAALGCLVK DYFPEPVTVS
              2    53
              *    **
         WNSGALTSGV

G3ch1    ASTKGPSVFP LAPCSRSTSG GTAALGCLVK DYFPEPVTVS
         WNSGALTSGV

G2ch1    ASTKGPSVFP LAPCSRSTSE STAALGCLVK DYFPEPVTVS
         WNSGALTSGV

G1ch1    ASTKGPSVFP LAPSSKSTSG GTAALGCLVK DYFPEPVTVS
         WNSGALTSGV 6                            7
                   *                            *
G4ch1    HTFPAVLQSS GLYSLSSVVT VPSSSLGTKT YTCNVDHKPS
              8
              *
         NTKVDKRV

G3ch1    HTFPAVLQSS GLYSLSSVVT VPSSSLGTQT YTCNVNHKPS
         NTKVDKRV

G2ch1    HTFPAVLQSS GLYSLSSVVT VPSSNFGTQT YTCNVDHKPS
         NTKVDKTV

G1ch1    HTFPAVLQSS GLYSLSSVVT VPSSSLGTQT YICNVNHKPS
         NTKVDKKV
```

FIG. 1B

OLIGO SEQUENCES -

Original sequences are in brackets.

| | Sequence | Surface property |
|---|---|---|
| *1* | (CG)<br>CTGAGTTCCAGCACACCGTCAC | Pocket |
| *2* | (CA)<br>TCAGGGCGCCGCAGTTCCACGA | Flat |
| *3* | (T)<br>TGCACGCCGCAGGTCAGGGCG | Convex |
| *4* | (CGT)<br>TCCACGACACGCACACCGGTTCG | Flat |
| *5* | (GT)<br>CACGCCGCTGCACAGGGCGCCT | Convex |
| *6* | (GT)<br>AGCCGGGAAGCAGTGCACGCCG | Pocket |
| *7* | (GT)<br>GCAGGTGTAGCACTTCGTGCCC | Flat |
| *8* | (GT)<br>GTCCACCTTGCAGTTGCTGGGC | Convex |

FIG. 2A

```
           10                  30                    50
GAATTCCCACTGACTCTAACCATGGAATGGAGCTGGGTCTTTCTCTTCTTCCTGTCAGTA
                        MetGluTrpSerTrpValPheLeuPhePheLeuSerVal 70                  90                   110
ACTACAGGTGTCCACTCCCAGGTTCAGCTGCAGCAGTCTGACGCTGAGTTGGTGAAACCT
ThrThrGlyValHisSerGlnValGlnLeuGlnGlnSerAspAlaGluLeuValLysPro 130                 150                   170
GGGGCTTCAGTGAAGATATCCTGCAAGGCTTCTGGCTACACCTTCACTGACCATGCTATT
GlyAlaSerValLysIleSerCysLysAlaSerGlyTyrThrPheThrAspHisAlaIle 190                 210                   230
CACTGGGCGAAGCAGAAGCCTGAACAGGGCCTGGAATGGATTGGATATATTTCTCCCGGA
HisTrpAlaLysGlnLysProGluGlnGlyLeuGluTrpIleGlyTyrIleSerProGly 250                 270                   290
AATGATGATATTAAGTACAATGAGAAGTTCAAGGGCAAGGCCACACTGACTGCAGACAAA
AsnAspAspIleLysTyrAsnGluLysPheLysGlyLysAlaThrLeuThrAlaAspLys 310                 330                   350
TCCTCCAGCACTGCCTACATGCAGCTCAACAGCCTGACATCTGAGGATTCTGCAGTGTAT
SerSerSerThrAlaTyrMetGlnLeuAsnSerLeuThrSerGluAspSerAlaValTyr 370                 390                   410
TTCTGTAAAAGATCGTACTACGGCCACTGGGGCCAAGGCACCACTCTCACAGTCTCCTCA
PheCysLysArgSerTyrTyrGlyHisTrpGlyGlnGlyThrThrLeuThrValSerSer
```

FIG. 2B

```
          10                  30                  50
ATCACACACACACACATGAGTGTGCCCACTCAGGTCCTGGGGTTGCTGCTGCTGTGGCTT
              MetSerValProThrGlnValLeuGlyLeuLeuLeuLeuTrpLeu 70                  90                 110
ACAGATGCCAGATGTGACATCCAGATGACTCAGTCTCCAGCCTCCCTATCTGTATCTGTG
ThrAspAlaArgCysAspIleGlnMetThrGlnSerProAlaSerLeuSerValSerVal 130                 150                 170
GGAGAAACTGTCACCATCACATGTCGAGCAAGTGAGAATATTTACAGTAATTTAGCATGG
GlyGluThrValThrIleThrCysArgAlaSerGluAsnIleTyrSerAsnLeuAlaTrp 190                 210                 230
TATCAACAGAAACAGGGAAAATCTCCTCAGCTCCTGGTCTATGCTGCAACAAACTTAGCA
TyrGlnGlnLysGlnGlyLysSerProGlnLeuLeuValTyrAlaAlaThrAsnLeuAla 250                 270                 290
GATGGTGTGCCATCAAGGTTCAGTGGCAGTGGATCGGGCACACAGTATTCCCTCAAGATC
AspGlyValProSerArgPheSerGlySerGlySerGlyThrGlnTyrSerLeuLysIle 310                 330                 350
AACAGCCTGCAGTCTGAAGATTTTGGGAGTTATTACTGTCAACATTTTTGGGGTACTCCG
AsnSerLeuGlnSerGluAspPheGlySerTyrTyrCysGlnHisPheTrpGlyThrPro 370                 390                 410
TACACGTTCGGAGGGGGGACCAGGCTGGAAATAAAACGGGCTGATGCTGCACCAACTGTC
TyrThrPheGlyGlyGlyThrArgLeuGluIleLysArgAlaAspAlaAlaProThrVal
```

RECOMBINANT ANTIBODIES AND METHODS FOR THEIR PRODUCTION IN WHICH SURFACE RESIDUES ARE ALTERED TO CYSTEINE RESIDUES FOR ATTACHMENT OF EFFECTOR OR RECEPTOR MOLECULES

The present invention relates to an altered antibody molecule having therein a specific thiol group for use in attachment to the antibody molecule of effector or reporter molecules and to a process for its production using recombinant DNA technology.

In the present application:

the term "MAb" is used to indicate a monoclonal antibody;

the term "recombinant antibody molecule" (RAM) is used to describe an antibody produced by any process involving the use of recombinant DNA technology, including any analogues of natural immunoglobulins or their fragments; and the term "humanised antibody molecule" (HAM) is used to describe a molecule having an antigen binding site derived from an immunoglobulin from a non-human species, the remaining immunoglobulin-derived parts of the molecule being derived from a human immunoglobulin. In a HAM the antigen binding site may comprise either complete variable domains fused onto constant domains or only the complementarity determining regions grafted onto appropriate framework regions in the variable domains.

In the description, reference is made to a number of publications by number. The publications are listed in numerical order at the end of the description.

Natural immunoglobulins have been known for many years, as have the various fragments thereof, such as the Fab, (Fab')$_2$ and Fc fragments, which can be derived by enzymatic cleavage. Natural immunoglobulins comprise a generally Y-shaped molecule having an antigen-binding site at the end of each arm. The remainder of the structure, and particularly the stem of the Y, mediates the effector functions associated with immunoglobulins.

Natural immunoglobulins have been used in diagnosis and, to a more limited extent, in therapy. However, such uses, especially in therapy, have been hindered by the polyclonal nature of natural immunoglobulins. A significant step towards the realisation of the potential of immunoglobulins as therapeutic agents was the discovery of monoclonal antibodies [1] of defined antigen specificity. Most MAbs are produced by fusions of rodent spleen cells with rodent myeloma cells. They are therefore essentially rodent MAbs. There are very few reports of the production of human MAbs.

There have been made proposals for making non-human MAbs less antigenic in humans. Such techniques can be generically termed "humanizing" MAbs. These techniques generally involve the use of recombinant DNA technology to manipulate DNA sequences encoding the polypeptide chains of the antibody molecule.

Some early methods for carrying out such a procedure are described in EP-A-0 71 496 (Res. Dev. Corp. Japan, EP-A-0 173 494 (Stanford University), EP-A-0 194 276 (Celltech Limited) and WO-A-8 702 671 (Int. Gen. Eng. Inc.).

In an alternative approach, described in EP-A-87302620.7 (Winter), the complementarity determining regions (CDRs) of a mouse MAb have been grafted onto the framework regions of the variable domains of a human immunoglobulin by site directed mutagenesis using long oligonucleotides.

It has been widely suggested that immunoglobulins, and in particular MAbs, could potentially be very useful in the diagnosis and treatment of cancer [2,3]. There has therefore been much activity in trying to produce immunoglobulins or MAbs directed against tumour-specific antigens. So far, over one hundred MAbs directed against a variety of human carcinomas have been used in various aspects of tumour diagnosis or treatment [4].

In our copending application Ser. No. 353,632 (ref; PA 149), also claiming priority from British patent application No. 8720833, there is described a humanised antibody molecule (HAM) having an antigen binding site wherein at least the complementarity determining regions (CDRs) of the variable domain are derived from the mouse monoclonal antibody B72.3 (B72.3 MAb) and the remaining immunoglobulin-derived parts of the HAM are derived from a human immunoglobulin. The B72.3 MAb is a mouse MAb of the type IgG1 raised against a membrane-enriched extract of a human liver metastatis of a breast carcinoma [5]. The B72.3 MAb has been extensively studied in a number of laboratories. It has been shown to recognise a tumour-associated glycoprotein TAG-72, a mucin-like molecule with a molecular weight of approximately $10^6$ [6]. Immunohistochemical studies have demonstrated that the B72.3 MAb recognises approximately 90% of colorectal carcinomas, 85% of breast carcinomas and 95% of ovarian carcinomas. However, it shows no significant cross-reactivity with a wide spectrum of normal human tissues [7 to 10].

In order to increase the efficacy of immunoglobulin molecules as diagnostic or therapeutic agents, it has been Proposed that effector or reporter molecules should be covalently linked thereto. However, this is not always possible to carry out conveniently. For instance, a potential site of attachment is a thiol group. Thiol groups occur naturally in proteins as cysteine residues. However, such residues are relatively uncommon, are often inside the molecule and are frequently involved in forming disulphide bridges within or between protein molecules. There is therefore a danger that, if any naturally occurring cysteine residue is used as a site of attachment, it will interfere with the normal folding and stabilization of the protein.

It has therefore been proposed that other side chains on a protein molecule be modified to produce a thiol group. For instance, lysine residues can be chemically modified to produce a thiol group on their side chains. However, this process will produce a thiol group on many or all available such lysine residues. It is therefore likely that there will be multiple possible attachment sites, making it impossible to determine in advance where any attachment will take place. Moreover, multiple attachment may cause interference with the biological activity of the protein. Further, with a number of extra thiol groups, it is possible that the new thiol groups will form inter- or intra-chain disulphide bonds which will alter the configuration and function of the protein.

It has also been proposed that the effector or reporter molecules may be attached by specific labelling of the carbohydrate moieties of immunoglobulins [11]. This generally involves periodate oxidation of the sugar residues to produce active aldehydes. However, this procedure has its disadvantages, in that the oxidation may also modify amino acids in the protein chains. For instance, methionine residues are readily oxidised. Moreover, the carbohydrate moieties are all located in the Fc portion of the immunoglobulin molecule. Therefore, it is not possible to use this method to label Fab or (Fab')$_2$ fragments of immunoglobulins.

It would therefore be desirable to provide a method by which effector or reporter molecules can be reproducibly and effectively attached to an immunoglobulin molecule in a site specific manner.

According to a first aspect of the present invention, there is provided an altered antibody molecule wherein a residue in a surface pocket on the molecule has been changed to a cysteine residue to introduce a thiol group in said surface pocket.

It will be understood by the skilled person that any protein molecule in its natural state adopts a folded configuration. Thus, the side chains of some of the amino acid residues are inside the folded protein and some are on the outside. Of those which are outside, some are located on convex surfaces, some on flat surfaces and some on concave surfaces. The concave surfaces are also described as pockets.

The skilled person would realise that the side chain of a residue on a flat or convex surface would probably protrude above the remainder of the protein. It would therefore be expected that, if such a residue were to be changed to a cysteine residue, the thiol group would be available for bonding to an effector or reporter molecule. Surprisingly, and contrary to this expectation, it has been found that if thiol groups are introduced in such positions, they are not available for such bonding. It would also be expected that a thiol group introduced as a side chain on an amino acid in a pocket would not be available for such bonding. However, surprisingly and contrary to this expectation, it has been found that such thiol groups are available and can be used to bond effector and reporter molecules to the antibody molecule. It may also have been expected that the introduction of such a thiol group would have grossly altered the macromolecular structure of the protein. Again, surprisingly and unexpectedly, it is found that this does not take place.

The altered antibody molecule of the present invention may comprise: a complete antibody molecule, having full length heavy and light chains; a fragment thereof, such as the Fab or (Fab')$_2$ fragment; or a light chain or heavy chain dimer so long as such a molecule has a thiol group introduced at a specified site and available for bonding.

In connection with this invention, "bonding" means forming covalent bonds to the thiol group of the cysteine residue.

It is envisaged that the altered antibody molecule may be produced by conventional peptide synthesis. However, it is preferred that the altered antibody molecule is produced by recombinant DNA technology.

According to a second aspect of the present invention, there is provided a process for altering the bonding ability of one chain of a recombinant antibody molecule, which process comprises:

(a) producing an expression vector which contains an operon encoding said one chain but in which the sequence encoding a preselected amino acid residue located in a surface pocket of the chain has been altered so that the amino acid residue encoded by the altered sequence is a cysteine residue.

If desired, two or more amino acid residues in a single polypeptide chain may be altered, or one or more amino acid residues in each of the two chains may be altered.

Preferably, the sequence alteration(s) is (are) carried out by site directed mutagenesis.

An essential feature of this aspect of the invention is the preselection of the position of the amino acid residue which is to be altered. Since it is desired to introduce a thiol group, as the side chain of a cysteine residue, to enable an effector or reporter molecule to be attached to the RAM, it is desirable that:

(i) the side chain of the amino-acid to be altered should be of a similar size to that of the cysteine residue:

(ii) there are no intra-chain hydrogen bonds with the residue to be altered:

(iii) there are no intra-chain hydrogen bonds which could form with the cysteine residue;

(iv) the thiol group should not be able to interact with or be hidden by any other parts of the RAM; and (v) the cysteine residue can only be accessed by small molecules, for instance of about 0.13 nm diameter, and not by molecules of larger size, for instance of greater than 0.5 nm diameter. Thus, the cysteine residue will only be available for bonding to the effector or reporter molecule and not to similar cysteine residues on the same or other chains.

The first three conditions will ensure, as far as possible, that the alteration to the new amino acid residue does not have any adverse effect on the conformation and stability of the RAM. The second two criteria ensure, as far as possible, that the thiol group will be available for bonding, but only to the effector or reporter molecule, and not to other similarly altered chains, thus preventing cross-linking by disulphide bonding. Residues which fulfil the requirement of (i) include threonine and serine. Thus, preferably, the residue(s) which is altered is a serine or threonine residue in a surface pocket of the immunoglobulin molecule.

A preferred site for carrying out such alteration is the CH1 domain, since alterations here and bonding of molecules thereto is unlikely to interfere with antigen binding or with the effector functions of the Fc portion (if present) of the altered antibody molecule. Advantageously, the residue in the CH1 domain which is altered is Ser 156 or Thr 173 (according to the numbering system set forth by Kabat et al. (14). However, suitable sites for alteration may be found in any of the domains of the antibody molecule.

Preferably, the process of the second aspect of the invention includes the steps of:

(b) transfecting a cell line with the vector; and (c) culturing the transfected cell line to produce a recombinant antibody molecule of altered bonding ability.

If desired, the antibody which is to be altered may be a "humanised" antibody produced by either of the methods referred to above In the process of the second aspect of the present invention, if the vector encodes only a single antibody polypeptide chain, the product of the process will be a dimeric molecule. If a tetrameric molecule, similar to a natural immunoglobulin, is required, one of two alternative strategies may be employed.

In the first alternative, the cell line may also be transfected with a second vector, the first vector encoding a heavy chain-derived polypeptide and the second vector encoding a complementary light chain-derived polypeptide. Preferably, the vectors are identical except in so far as the coding sequences and selectable markers are concerned so as to ensure as far as possible that each polypeptide chain is equally expressed.

In the second alternative, the vector may include sequences coding for complementary light chain- and heavy chain-derived polypeptides.

If the vector encodes only a heavy chain polypeptide, it is also possible to produce a recombinant antibody molecule by using a host cell which naturally secretes a complementary light chain.

The present invention also includes cloning and expression vectors and transfected cell lines used in the process of the invention, therapeutic and diagnostic compositions containing the altered molecule of the invention and uses of such compositions in therapy and diagnosis.

Reporter or effector molecules may be attached to the altered antibody molecule by any convenient method. For instance, a method for attaching a radiolabel to an antibody is described in our earlier British patent applications Nos. 8800843 and 8812257.

The general methods by which the vectors may be constructed, transfection methods and culture methods are well known per se and form no part of the invention. Such methods are shown, for instance, in references 12 and 13.

The present invention is now described, by way of example only, with reference to the accompanying drawings in which:

FIGS. 1A and 1B show the DNA and amino acid sequence of the B72.3 HAM CH1 domain of a humanized B72.3 antibody molecule together with the sequences of 8 oligonucleotide primers used for site directed mutagenesis; and FIGS. 2A and 2B show the DNA sequences encoding the unprocessed variable regions of the B72.3 MAb obtained by sequencing the cDNA clones pBH41 and pBL52. Panel A shows the sequence coding for the VH region and the predicted amino acid sequence. Panel B shows the sequence coding for the VL region and the first 21 residues of the CL region, together with the predicted amino acid sequence. The points of fusion with the human C regions are indicated with arrows. The putative sites of cleavage of the signal peptide are indicated by open triangle. The numbers refer to the nucleotides in the original cDNA clones.

In our copending application Ser. No. 353,632, now abandoned, (PA149) referred to above, there is described the production of humanised B72.3 MAbs having various human IgG heavy chain domains. The application also shows the production of humanised B72.3 F(ab')$_2$ fragments. The results set out hereafter were obtained by use of the humanised B72.3 MAbs obtained as described below.

Molecular Cloning and Sequence of the B72.3 Heavy and Light Chain cDNAs

Polyadenylated RNA was isolated from the B72.3 hybridoma cell line using the guanidinium isothicyanate/cesium chloride method (12). Double stranded cDNA was synthesized (18) and a cDNA library was constructed in bacteriophage λgt10 vector using EcoRI linkers (19). Two screening probes were synthesized, complementary to mouse immunoglobulin heavy and light chain constant regions. The heavy chain probe was 19 mer complementary to residues 115–133 in the CH1 domain of the mouse τ1 sequence (20). The light chain probe was a 20 mer complementary to residues 4658–4677 of the genomic mouse CK sequence (21). The probes were radio-labelled at the 5' terminus with [τ $^{32}$P] ATP using T4 polynucleotide kinase (Amersham International) and used to screen the cDNA library.

Clones which contained the complete leader, variable and constant regions of both the heavy and light chains were isolated. The EcoRI cDNA inserts were subcloned into M13mp8 vectors for sequencing (22), generating a heavy chain clone, designated pBH41, and a light chain clone, designated pBL52. Nucleotide sequence analysis was carried out according to the chain termination procedure (16).

The 980 base pair EcoRI insert in pBL52 was fully sequenced (16). The EcoRI insert in pBH41 was shown to comprise approximately 1700 base pairs by agarose gel electrophoresis. The variable domain and the 5' region of the CH1 domain were sequenced, as was the 3' end of the clone to confirm the presence of the correct mouse τ1 termination sequences. The DNA and predicted amino acid sequences for the unprocessed variable regions of pBH41 and pBL52 are shown in FIG. 2. Examination of the derived amino acid sequence revealed considerable homology with other characterized immunoglobulin genes, and enabled the extent of the leader, variable and constant domains to be accurately determined. In addition, MAb B72.3 was confirmed to be an IgG1 K antibody, as previously reported (5).

Construction of the Chimeric Mouse-Human Heavy Chain Clone

A genomic clone containing sequences coding for the human cτ4 region was isolated as a HindIII fragment from the cosmid COS Ig8 (23) and then cloned via pAT153 into M13tg130 as an EcoRI-BamHI fragment to form pJA78. Following DNA sequence analysis, an 18 mer oligonucleotide was synthesized and site specific mutagenesis was performed to convert a C residue to an A residue, thereby generating a novel HindIII site at the start of the CH1 exon, to yield pJA91.

Site directed mutagenesis was performed (24) using EcoRI- and BglI-cut M13mp18 to generate a gapped duplex with the relevant phage template. DNA was transformed into E. coli HB2154 and resultant transformants were propagated on E. coli HB2151 (Anglian Biotechnology Ltd) as described in the protocols provided. All mutations were sequenced using the chain termination procedure (16). All sequenced fragments were subsequently recloned mutations which may have occurred during the mutagenesis procedure.

The VH domain from the B72.3 heavy chain cDNA, cloned in M13mp9 as pBH41, was isolated as an EcoRI-BglI fragment and introduced into the EcoRI-HindIII sites of pJA91 in conjunction with a 32 base pair BglI-HindIII adapter to yield pJA93. The product was, therefore, a chimeric immunoglobulin heavy gene containing a variable region derived from a mouse cDNA clone fused to a sequence, comprising the CH1, H, CH2 and CH3 domains separated by introns, derived form a human genomic clone. The accuracy of the variable/constant region junction was confirmed by nucleotide sequence analysis.

Construction of the Chimeric Mouse-Human Light Chain Gene

The mouse light chain cDNA clone, pBL52, contains a cutting site for MboII 18 base pairs downstream from the junction of the variable and constant domains. Due to sequence homology between the mouse and human CK genes, an identical cutting site exists in the latter gene (25) and use of this site provides a method of fusing the mouse variable and human constant domains. Partial digestion of the EcoRI fragment containing the mouse cDNA clone with MboII generated a 416 base pair EcoRI-MboII fragment with a single residue overhang. A genomic clone, comprising an M13-derived vector containing the human C-kappa gene on a PstI-HindIII fragment was digested with FokI. A 395 base pair fragment containing the majority of C-kappa was cloned into pAT153 using EcoRI linkers to form pNW200. Digestion of a 945 base pair ScaI-HindIII fragment, which could anneal with and be ligated to the 416 base pair ECoRI-MboII fragment described above. The two fragments were ligated into a pSP64 vector linearized with EcoRI and HindIII, and used to transform competent E. coli HB101. The variable/constant region junction was sequenced in order to confirm the correct fusion.

Construction of Expression Vectors for Transient Expression in COS Cells

The heavy and light chain chimeric genes, as well as the mouse heavy and light chain cDNA clones, were inserted separately into the unique EcoRI site of plasmid pEE6 (17). The light chain encoding plasmid was designated EE6.cL.neo. For the chimeric heavy chain, this was accomplished by using an oligonucleotide adapter to chain the 3' BamHI site to an EcoRI site to give an EcoRI fragment for cloning. The heavy chain encoding plasmid was designated EE6.cH.gpt. (also designated as JA96). this plasmid contains the strong promoter/enhancer and transcriptional control element from the human cytomegalovirus (hCMV) inserted into a unique HindIII site upstream of the EcoRI site. In addition, an SV40 origin of replication site is provided by the SV40 early promoter which drives a selectable marker gene, either a neomycin-resistance gene (neo) for light chain gene or a guanine phosphoribosyl transferase gene (gpt) for heavy chain genes, inserted into a unique BamHI site. The plasmid also contains an ampicillin-resistance gene allowing selection and propagation in bacterial hosts.

Expression of the heavy and light chain genes from the above plasmids leads to the production of the humanized antibody molecules referred to herein.

The nucleotide sequence and amino acid sequence of the CH1 domain of the humanised B72.3 molecule is shown in the drawing, to which reference is now made. In order to enable the humanised B72.3 antibody molecule to be bound to an effector or reporter molecule via a covalent linkage, a search was carried out for any serine or threonine residues located in a surface pocket and which satisfied the criteria set out as (i) to (v) previously. For the sake of comparison, other serine or threonine residues not meeting all the criteria were also selected.

The CH1 domain of the B72.3 molecule shows considerable sequence homology with that of the human antibody KOL. The KOL antibody is described by Kabat et al. (14). A crystal structure for the KOL antibody has been determined by x-ray cyrstallography. By making the necessary amino acid substitutions, it is possible to predict the structure of the B72.3 CH1 domain on the basis of the structure of the KOL CH1 domain.

On the basis of this prediction, a number of serine and threonine residues were selected. All were predicted to be located on the surface of the humanized B72.3 molecule, but it was predicted that some would be in pockets, some on flat surfaces and some on convex surfaces. The target residues were identified as Thr 153; Ser 156; Ser 163; Thr 167; Ser 68; Thr 173; Thr 205; and Thr 217. The residue numbering used herein corresponds to that set forth by Kabat et al. (14).

Oligonucleotide primers for use in site directed mutagenesis experiments according to the gapped—duplex method (15) were produced. These are shown in the drawing. In each case, the primer was designed to effect a change of one of the above threonine or serine residues to a cysteine residue. The altered DNA vectors have now been produced and sequenced by the chain termination procedure (16).

All altered gene fragments were subsequently re-cloned into plasmid PEE6.HCMV (17) for expression in mammalian cell systems. This plasmid contains the strong promoter/enhancer transcriptional control element from human cytomegalovirus (17). Five of the original eight proposed cysteine mutants, namely numbers 1, 3, 4, 6 and 7, were taken to this stage.

The synthesis and functional assembly of the altered humanised B72.3 antibodies were analysed by transient expression in COS cells (17). Each of the five heavy chain mutant genes were transfected into the cells together with the humanised B72.3 light chain gene. Cell supernatants were assayed for B72.3 antigen binding activity using an ELISA assay. Secretion and assembly of immunogloublins was also evaluated by biosynthetic labelling and immunoprecipitation of the transfected COS cells. The results of both types of analysis showed that all five thiol mutant genes produced fully assembly tetrameric antibody molecules whose antigen binding properties were indistinguishable from the unaltered humanised B72.3 molecule. None of the mutants appeared to producd aggregated molecules.

The transient expression system did not produce sufficient amounts of the antibodies for more detailed biochemical characterisation. Thus stable cell lines expressing the modified B72.3 antibodies were established. The mutant heavy chain genes were transfected by electroporation into a chinese hamster ovary (CHO) cell line which already produced the humanised B72.3 light chain. Transfected cell lines were selected using a drug resistance marker incorporated into the pEE6.HCMV plasmid and cells producing altered B72.3 antibody were cloned and expanded.

Recombinant antibodies (both unmodified and thiol mutants) were purified from CHO cell supernatants by affinity chromatography on protein A-sepharose and concentrated by ultrafiltration. Purified antibodies were shown to be fully assembled and non-aggregated by SDS-polyacrylamide gel electrophoresis and gel filtration HPLC, confirming the results of the transient expression experiments. Antigen binding was demonstrated by ELISA. Collectively these results showed that substituting single cysteine residues at the surface of the CH1 domain of the heavy chain had not affected the synthesis, assembly and antigen binding activities of the altered antibodies. This appeared to be irrespective of the topographical position of the introduced thiol since all the mutants analysed behaved the same.

Since each immunoglobulin molecule comprises two heavy chains, the altered antibodies should have two free thiols if the cysteines remained in a reduced form.

The redox state of the surface cysteines was measured by titration using 4,4'-dithiodipyridine. Antibody samples (0.5 mg/ml) were added to 4,4'-dithiopyridine (0.5 mM final concentration) and reaction with free thiol groups was monitored by an increase in absorbance at 324 nm. The results are summarised in the following table

| Titration of free-SH groups on humanised B72.3 thiol mutants. | | |
|---|---|---|
| Mutant No. | Position | No. free thiols |
| 1 | pocket | 0.97 |
| 3 | convex | 0.30 |
| 4 | flat | 0.30 |
| 6 | pocket | 1.10 |
| 7 | flat | 0.30 |
| B72.3 | control | 0.30 |

Mutants 3, 4 and 7 have approximately the same values for the number of free thiol groups as the unaltered humanised B72.3 control, indicating that the introduced cysteines are not available for bonding. It is conjectured that they are most probably blocked in some way, for example by reaction with glutathione in vivo or in vitro. On the other hand, mutants 1 and 6 gave titration levels significantly greater than the control, corresponding to at least one free thiol group per antibody molecule. The discrepancy between this and the expected value of two thiols per antibody suggested that some oxidation of the thiols may have occurred.

However, the results showed that cysteines positioned at flat (mutants 4 and 7) or convex (mutant 3) surfaces, i.e. with relatively high contact surface accessibility, would not be suitable for site-specific attachment since their thiol groups appear to be blocked. By contrast the two cysteines located in pocket sites (mutants 1 and 6) remain in a form available for bonding to the extent of at least one free thiol per antibody molecule.

To investigate whether the mutants shown to have free thiols could be used for site-specific attachment of a reporter or effector molecule, a thiol specific linker was synthesised. Tyrosineamide (0.1 mmol in 0.5M pipes buffer, pH 6.8) was reacted with N-succinimidyl-3-maleimidopropionate .0.015 mmol in 1,4-dioxane) to give 2-(3-N-malemidyl)—N-propylamido-3-(4-hydroxy)phenylpropanoamide. This ligand is referred to as tyrosine maleimide and was labelled with $^{125}$Iodine using chloramine T. The radioactive compound was purified by reverse phase HPLC. One of the thiol mutants (No. 6) was incubated with the iodinated probe (1 h, pH 5.5 at room temp.). Labelled antibody was separated from unincorporated ligand by either gel filtration or protein A-sepharose precipitation and analysed by SDS-polyacrylamide gel electrophoresis/autoradiography. Both humanised and hybridoma-derived mouse B72.3 were included as negative controls.

Humanised B72.3 that had been reacted with 2-iminothiolane, which non-selectively introduces thiol groups onto lysine residues, was used as a positive control for the labelling procedure. The results of this analysis showed as expected that the thiol specific ligand tyrosine maleimide only labelled the heavy chain of the thiol mutant B72.3. By contrast the non-specifically modified humanised B72.3 was labelled on both heavy and light chains and also produced a number of aggregated molecules. Thus the site-specifically labelled antibody produced a more homogeneous product.

The process described above shows that cysteine residue may be substituted into the heavy chain of an antibody molecule in such a position that reporter molecule may be site-specifically attached to that antibody molecule through the introduced thiol. It shows that the thiol group must be introduced into a surface pocket in order for it to be able effectively to bond to the effector or reporter molecule.

It will be appreciated that the same procedure may be carried out on a different domain of the heavy or light chain of an antibody molecule. All that is necessary is to locate a suitable surface pocket site having therein an appropriate amino acid residue.

It will be appreciated that the present invention has been described above by way of illustration only, and that variations or modifications of detail can be made without departing from the scope of the invention.

REFERENCES

1. Kohler & Milstein, Nature, 265, 495–497, 1975.
2. Ehrlich, P., Collected Studies on Immunity, 2, John Wiley & Sons, New York, 1906.
3. Levy & Miller, Ann.Rev.Med., 34, 107–116, 1983.
4. Schlom & Weeks, Important Advances in Oncology, 170–192, Wippincott, Philadelphia, 1985.
5. Colcher et al., PNAS, 78, 3199–3203, 1981.
6. Johnson et al., Cancer Res., 46, 850–897, 1986.
7. Stramignoni et al., Int.J.Cancer, 31, 543,552, 1983.
8. Nuti et al., Int.J.Cancer, 29, 539–545, 1982.
9. Thor et al., J.Nat.Cancer Inst., 76, 995–1006, 1986.
10. Thor et al., Cancer Res., 46, 3118–3124, 1986.
11. O'Shannessy & Quarles, J. Immunol. Methods, 99, 153–161, 1987.
12. Maniatis et al., Molecular Cloning, Cold Spring Harbor, New York, 1982.
13. Primrose and Old, Principles of Gene Manipulation, Blackwell, Oxford, 1980.
14. Kabat et al.,Sequences of Proteins of Immunological Interest, Fourth Edition, U.S. Dept. of Health and Human Services, 1987.
15. Boshart et al., Cell; 41, 521–530, 1985.
16. Sanger et al., PNAS, 74, 5463–5467, 1977.
17. Whittle et al., Prot. Eng., 1, 6, 499–530, 1985
18. Gubler and Hoffman, gene, 25, 263–269, 1983.
29. Huynh et al., Practical Advances in Biochemistry, IRL, Oxford (Ed. Glover, M.M.), 1984.
20. Honjo et al., Cell, 18, 559–568, 1979.
21. Max et al., J. Biol. Chem., 256, 5116–5120, 1981.
22. Messing and Vieira, Gene, 19, 269–276, 1982.
23. Krawinkel and Rabbits, EMBO J., 1, 403–407, 1982.
24. Kramer et al, Nuc. Acids Res., 12, 9441–9446, 1984.
25. Heiter et al., Cell, 22, 197–207, 1980.

We claim:

1. An altered antibody molecule wherein an amino acid residue in a surface pocket on the molecule has been changed to a cysteine residue to introduce a thiol group in said surface pocket, such that said cysteine residue can only be accessed by small molecules of about 0.13 to 0.5 nm in diameter and such that said cysteine residue is only available for bonding to an effector or reporter molecule and not to a cysteine residue on the same or other antibody chains.

2. The altered antibody molecule of claim 1, made by recombinant DNA technology.

3. The altered antibody molecule of claim 1, which is a complete antibody molecule, an Fab fragment or an F(ab')$_2$ fragment.

4. The altered antibody molecule of any one of claims 1 to 3, wherein the alteration is in the CH1 domain.

5. The altered antibody molecule of claim 4, wherein the amino acid residue which has been changed is Ser 156 or Thr 173.

6. A process for providing the altered antibody of claim 1 which process comprises:
   (a) producing an expression vector which contains an operon encoding one immunoglobulin chain but in which the sequence encoding a preselected amino acid residue located in the surface pocket of the chain has been altered so that the amino acid residue encoded by the altered sequence is a cysteine residue.

7. The process of claim 6, in which the alteration is carried out by site directed mutagenesis.

8. The process of claim 6 or claim 7, further including the steps of:
   (b) transfecting a cell line with the vector; and
   (c) culturing the transfected cell line to produce a recombinant antibody molecule of altered bonding ability.

9. The process of claim 8, wherein the cell line is also transformed with a second vector, the first vector encoding a heavy chain-derived polypeptide and the second vector encoding a complementary light-chain derived polypeptide.

10. The process of claim 8, wherein the expression vector includes sequences coding for complementary light- and heavy- chain derived polypeptides.

* * * * *